(12) United States Patent
Gong et al.

(10) Patent No.: US 11,028,172 B1
(45) Date of Patent: Jun. 8, 2021

(54) ANTI-TIGIT ANTIBODIES AND USES THEREOF

(71) Applicant: Lepu Biopharma Co., Ltd., Shanghai (CN)

(72) Inventors: Wenci Gong, Shanghai (CN); Yiwei Tou, Beijing (CN)

(73) Assignee: Lepu Biopharma Co., Ltd., Shanghai (CN)

(*) Notice: Subject to any disclaimer, the term of this patent is extended or adjusted under 35 U.S.C. 154(b) by 0 days.

(21) Appl. No.: 17/117,969

(22) Filed: Dec. 10, 2020

(30) Foreign Application Priority Data

Nov. 10, 2020 (WO) ................ PCT/CN2020/127710

(51) Int. Cl.
*C07K 16/28* (2006.01)
*A61P 35/00* (2006.01)
*A61K 39/00* (2006.01)

(52) U.S. Cl.
CPC .......... *C07K 16/2809* (2013.01); *A61P 35/00* (2018.01); *A61K 2039/505* (2013.01); *C07K 2317/24* (2013.01); *C07K 2317/31* (2013.01); *C07K 2317/55* (2013.01); *C07K 2317/565* (2013.01); *C07K 2317/622* (2013.01); *C07K 2317/732* (2013.01)

(58) Field of Classification Search
None
See application file for complete search history.

(56) References Cited

U.S. PATENT DOCUMENTS

| 2016/0176963 A1* | 6/2016 | Maurer | C07K 16/2803 424/139.1 |
|---|---|---|---|
| 2016/0355589 A1* | 12/2016 | Williams | A61P 35/00 |
| 2018/0155422 A1* | 6/2018 | Bhatt | C07K 16/2803 |

* cited by examiner

*Primary Examiner* — Nelson B Moseley, II
(74) *Attorney, Agent, or Firm* — Sheppard Mullin Richter & Hampton LLP

(57) ABSTRACT

Provided are anti-TIGIT antibodies and fragments thereof. The antibodies and fragments thereof specifically bind to the TIGIT protein. Methods of using the antibodies or fragments thereof for treating and diagnosing diseases such as cancer and viral infections are also provided.

20 Claims, 7 Drawing Sheets

Specification includes a Sequence Listing.

SEQUENCE LISTING

<160> NUMBER OF SEQ ID NOS: 18

<210> SEQ ID NO 1
<211> LENGTH: 6
<212> TYPE: PRT
<213> ORGANISM: Artificial Sequence
<220> FEATURE:
<223> OTHER INFORMATION: Synthetic

<400> SEQUENCE: 1

Ser Gly Tyr Asp Trp His
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic

<400> SEQUENCE: 2

Phe Ile Arg Asp Ser Gly Ser Thr Val Tyr Asn Pro Ser Leu Lys Gly
1               5                   10                  15

<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3

Gly Leu Phe Trp Tyr Phe Asp Val
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Arg Thr Ser Glu Asn Ile Phe Ser Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Asn Thr Lys Thr Leu Ala Glu
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Gln His His Tyr Gly Asn Pro Leu Thr
1               5

```
<210> SEQ ID NO 7
<211> LENGTH: 117
<212> TYPE: PRT
<213> ORGANISM: Artificial Sequence
<220> FEATURE:
<223> OTHER INFORMATION: Synthetic

<400> SEQUENCE: 7

Asp Val Gln Leu Gln Glu Ser Gly Pro Gly Met Val Lys Pro Ser Gln
1               5                   10                  15

Ser Leu Ser Leu Thr Cys Thr Ala Thr Gly Tyr Ser Ile Thr Ser Gly
            20                  25                  30

Tyr Asp Trp His Trp Ile Arg His Phe Pro Gly Lys Lys Leu Glu Trp
        35                  40                  45

Met Gly Phe Ile Arg Asp Ser Gly Ser Thr Val Tyr Asn Pro Ser Leu
    50                  55                  60

Lys Gly Arg Ile Ser Ile Thr His Asp Thr Ser Lys Asn Arg Phe Phe
65                  70                  75                  80

Leu Lys Leu Asn Ser Val Thr Pro Glu Asp Thr Ala Thr Tyr Phe Cys
                85                  90                  95

Ala Arg Gly Leu Phe Trp Tyr Phe Asp Val Trp Gly Thr Gly Thr Thr
            100                 105                 110

Val Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Synthetic

<400> SEQUENCE: 8

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Ile Phe Ser Tyr
            20                  25                  30

Leu Ala Trp Tyr Gln Gln Lys Gln Gly Asn Ser Pro Gln Leu Leu Val
        35                  40                  45

His Asn Thr Lys Thr Leu Ala Glu Gly Val Pro Ser Arg Phe Ser Gly
    50                  55                  60

Ser Gly Ser Gly Thr Gln Phe Ser Leu Lys Ile Ser Asn Leu Gln Pro
65                  70                  75                  80

Glu Asp Phe Gly Ser Tyr Tyr Cys Gln His His Tyr Gly Asn Pro Leu
                85                  90                  95

Thr Phe Gly Ala Gly Thr Lys Leu Glu Leu Lys
            100                 105

<210> SEQ ID NO 9
<211> LENGTH: 117
<212> TYPE: PRT
<213> ORGANISM: Artificial Sequence
<220> FEATURE:
<223> OTHER INFORMATION: Synthetic

<400> SEQUENCE: 9

Glu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30
```

```
Tyr Asp Trp His Trp Ile Arg Gln Pro Pro Gly Lys Gly Leu Glu Trp
                35                  40                  45

Ile Gly Phe Ile Arg Asp Ser Gly Ser Thr Val Tyr Asn Pro Ser Leu
 50                  55                  60

Lys Gly Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Leu Phe Trp Tyr Phe Asp Val Trp Gly Gln Gly Thr Thr
                100                 105                 110

Val Thr Val Ser Ser
            115

<210> SEQ ID NO 10
<211> LENGTH: 117
<212> TYPE: PRT
<213> ORGANISM: Artificial Sequence
<220> FEATURE:
<223> OTHER INFORMATION: Synthetic

<400> SEQUENCE: 10

Glu Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Ser Ser Gly
                 20                  25                  30

Tyr Asp Trp His Trp Ile Arg Gln Pro Pro Gly Lys Gly Leu Glu Trp
                 35                  40                  45

Ile Gly Phe Ile Arg Asp Ser Gly Ser Thr Val Tyr Asn Pro Ser Leu
 50                  55                  60

Lys Gly Arg Val Thr Ile Ser His Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Leu Phe Trp Tyr Phe Asp Val Trp Gly Gln Gly Thr Thr
                100                 105                 110

Val Thr Val Ser Ser
            115

<210> SEQ ID NO 11
<211> LENGTH: 117
<212> TYPE: PRT
<213> ORGANISM: Artificial Sequence
<220> FEATURE:
<223> OTHER INFORMATION: Synthetic

<400> SEQUENCE: 11

Glu Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Ser Ser Gly
                 20                  25                  30

Tyr Asp Trp His Trp Ile Arg Gln Pro Pro Gly Lys Gly Leu Glu Trp
                 35                  40                  45

Ile Gly Phe Ile Arg Asp Ser Gly Ser Thr Val Tyr Asn Pro Ser Leu
 50                  55                  60

Lys Gly Arg Ile Thr Ile Ser His Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95
```

```
Ala Arg Gly Leu Phe Trp Tyr Phe Asp Val Trp Gly Gln Gly Thr Thr
                100                 105                 110
Val Thr Val Ser Ser
        115

<210> SEQ ID NO 12
<211> LENGTH: 117
<212> TYPE: PRT
<213> ORGANISM: Artificial Sequence
<220> FEATURE:
<223> OTHER INFORMATION: Synthetic

<400> SEQUENCE: 12

Glu Val Gln Leu Gln Glu Ser Gly Pro Gly Leu Val Lys Pro Ser Glu
1               5                   10                  15
Thr Leu Ser Leu Thr Cys Ala Val Ser Gly Tyr Ser Ile Ser Ser Gly
            20                  25                  30
Tyr Asp Trp His Trp Ile Arg Gln Pro Pro Gly Lys Gly Leu Glu Trp
        35                  40                  45
Met Gly Phe Ile Arg Asp Ser Gly Ser Thr Val Tyr Asn Pro Ser Leu
    50                  55                  60
Lys Gly Arg Ile Thr Ile Ser His Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Gly Leu Phe Trp Tyr Phe Asp Val Trp Gly Gln Gly Thr Thr
                100                 105                 110
Val Thr Val Ser Ser
        115

<210> SEQ ID NO 13
<211> LENGTH: 117
<212> TYPE: PRT
<213> ORGANISM: Artificial Sequence
<220> FEATURE:
<223> OTHER INFORMATION: Synthetic

<400> SEQUENCE: 13

Glu Val Gln Leu Gln Glu Ser Gly Pro Gly Leu Val Lys Pro Ser Glu
1               5                   10                  15
Thr Leu Ser Leu Thr Cys Ala Ser Gly Tyr Ser Ile Thr Ser Gly
            20                  25                  30
Tyr Asp Trp His Trp Ile Arg Gln Pro Pro Gly Lys Gly Leu Glu Trp
        35                  40                  45
Met Gly Phe Ile Arg Asp Ser Gly Ser Thr Val Tyr Asn Pro Ser Leu
    50                  55                  60
Lys Gly Arg Ile Thr Ile Ser His Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Gly Leu Phe Trp Tyr Phe Asp Val Trp Gly Gln Gly Thr Thr
                100                 105                 110
Val Thr Val Ser Ser
        115

<210> SEQ ID NO 14
<211> LENGTH: 117
<212> TYPE: PRT
<213> ORGANISM: Artificial Sequence
```

```
<220> FEATURE:
<223> OTHER INFORMATION: Synthetic

<400> SEQUENCE: 14

Glu Val Gln Leu Gln Glu Ser Gly Pro Gly Leu Val Lys Pro Ser Glu
1               5                   10                  15

Thr Leu Ser Leu Thr Cys Ala Ala Ser Gly Tyr Ser Ile Thr Ser Gly
            20                  25                  30

Tyr Asp Trp His Trp Ile Arg Gln Pro Pro Gly Lys Lys Leu Glu Trp
        35                  40                  45

Met Gly Phe Ile Arg Asp Ser Gly Ser Thr Val Tyr Asn Pro Ser Leu
    50                  55                  60

Lys Gly Arg Ile Thr Ile Ser His Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Arg Gly Leu Phe Trp Tyr Phe Asp Val Trp Gly Gln Gly Thr Thr
            100                 105                 110

Val Thr Val Ser Ser
        115

<210> SEQ ID NO 15
<211> LENGTH: 107
<212> TYPE: PRT
<213> ORGANISM: Artificial Sequence
<220> FEATURE:
<223> OTHER INFORMATION: Synthetic

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Phe Ser Tyr
            20                  25                  30

Leu Ala Trp Tyr Gln Gln Lys Pro Gly Lys Val Pro Lys Leu Leu Ile
        35                  40                  45

Tyr Asn Thr Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His His Tyr Gly Asn Pro Leu
                85                  90                  95

Thr Phe Gly Gln Gly Thr Lys Leu Glu Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: Synthetic

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Phe Ser Tyr
            20                  25                  30

Leu Ala Trp Tyr Gln Gln Lys Pro Gly Lys Val Pro Lys Leu Leu Ile
        35                  40                  45
```

```
His Asn Thr Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln His His Tyr Gly Asn Pro Leu
                 85                  90                  95

Thr Phe Gly Gln Gly Thr Lys Leu Glu Ile Lys
                100                 105
```

<210> SEQ ID NO 17
<211> LENGTH: 107
<212> TYPE: PRT
<213> ORGANISM: Artificial Sequence
<220> FEATURE:
<223> OTHER INFORMATION: Synthetic

<400> SEQUENCE: 17

```
Asp Ile Gln Met Thr Gln Ser Pro Ser Ser Leu Ser Ala Ser Val Gly
 1               5                  10                  15

Asp Arg Val Thr Ile Thr Cys Arg Thr Ser Glu Asn Ile Phe Ser Tyr
                 20                  25                  30

Leu Ala Trp Tyr Gln Gln Lys Pro Gly Lys Val Pro Lys Leu Leu Val
             35                  40                  45

His Asn Thr Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln His His Tyr Gly Asn Pro Leu
                 85                  90                  95

Thr Phe Gly Gln Gly Thr Lys Leu Glu Ile Lys
                100                 105
```

<210> SEQ ID NO 18
<211> LENGTH: 107
<212> TYPE: PRT
<213> ORGANISM: Artificial Sequence
<220> FEATURE:
<223> OTHER INFORMATION: Synthetic

<400> SEQUENCE: 18

```
Asp Ile Gln Met Thr Gln Ser Pro Ser Ser Leu Ser Ala Ser Val Gly
 1               5                  10                  15

Asp Arg Val Thr Ile Thr Cys Arg Thr Ser Glu Asn Ile Phe Ser Tyr
                 20                  25                  30

Leu Ala Trp Tyr Gln Gln Lys Pro Gly Lys Val Pro Lys Leu Leu Val
             35                  40                  45

His Asn Thr Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln His His Tyr Gly Asn Pro Leu
                 85                  90                  95

Thr Phe Gly Gln Gly Thr Lys Leu Glu Ile Lys
                100                 105
```

ANTI-TIGIT ANTIBODIES AND USES THEREOF

CROSS REFERENCE TO RELATED APPLICATIONS

This application claims priority to PCT/CN2020/127710, filed Nov. 10, 2020, which is hereby incorporated by reference in its entirety.

SEQUENCE LISTING

The instant application contains a Sequence Listing which has been filed electronically in ASCII format and is hereby incorporated by reference in its entirety. Said ASCII copy, created on Dec. 9, 2020, is named 320294US ST25.txt and is 16,384 bytes in size.

BACKGROUND

The T cell immunoreceptor with Ig and ITIM domains (TIGIT) protein is a member of the PVR (poliovirus receptor) family of immunoglobin proteins. It is expressed on several classes of T cells including follicular B helper T cells (TFH). TIGIT has been shown to bind PVR with high affinity and the binding is thought to assist interactions between TFH and dendritic cells to regulate T cell dependent B cell responses.

TIGIT is a member of the immunoglobulin superfamily with an immunoreceptor tyrosine-based inhibitory motif (ITIM) in the cytoplasmic tail, and is expressed on subsets of activated T cells and natural killer (NK) cells. TIGIT is known to interact with CD155 (also called PVR and necl-5), CD112 (also called PVRL2 and nectin-2), and possibly CD113 (also called PVRL3 and nectin-3). Binding of TIGIT with a high affinity ligand CD155, which are expressed on antigen-presenting cells, has been reported to suppress the function of T cells and NK cells. TIGIT has also been reported to inhibit T cells indirectly by modulating cytokine production by dendritic cells.

Tumors constitute highly suppressive microenvironments where infiltrating T cells are exhausted and NK cells are silenced by checkpoint molecules such as PD-1 and TIGIT to evade from the immune responses. A high-level expression of TIGIT on CD8+ T cells has been reported to correlate with poor clinical outcomes of AML subjects. The functional defects of exhausted TIGIT+CD8+ T cells from AML subjects were reported to be reversed by the siRNA-mediated knockdown of TIGIT expression. It has also been reported that effector CD8+ T cells during HIV infection in blood and SIV infection in lymphoid tissue exhibit higher levels of TIGIT.

TIGIT is also involved in viral infections. During Human Immunodeficiency Virus (HIV) infection, TIGIT expressing CD8+ T cells has been shown to be expanded and associated with clinical markers of HIV disease progression in a diverse group of HIV infected individuals. Elevated TIGIT levels remained sustained even among those with undetectable viral loads and a large fraction of HIV-specific CD8+ T cells simultaneously express both TIGIT and another negative checkpoint receptor, Programmed Death Protein 1 (PD-1) and retained several features of exhausted T cells. Blocking these pathways with targeted monoclonal antibodies can rejuvenat HIV-specific CD8+ T cell responses. This pathway can potentially be targeted to enhance killing of HIV infected cells during "Shock and Kill" HIV curative approaches.

SUMMARY

The present disclosure provides antibodies and antigen-binding fragments specific to the human TIGIT protein which can be used for treating various cancers and other diseases, such as viral infections.

One embodiment of the present disclosure provides an antibody or fragment thereof, wherein the antibody or fragment thereof has specificity to a T cell immunoreceptor with Ig and ITIM domains (TIGIT) protein and comprises a heavy chain variable region (VH) comprising a VH CDR1 comprising the amino acid sequence of SEQ ID NO:1, a VH CDR2 comprising the amino acid sequence of SEQ ID NO:2, and a VH CDR3 comprising the amino acid sequence of SEQ ID NO:3, and a light chain variable region (VL) comprising a VL CDR1 comprising the amino acid sequence of SEQ ID NO:4, a VL CDR2 comprising the amino acid sequence of SEQ ID NO:5, and a VL CDR3 comprising the amino acid sequence of SEQ ID NO:6.

In some embodiments, the VH comprises an amino acid sequence selected from the group consisting of SEQ ID NO:9-14 and the VL comprises an amino acid sequence selected from the group consisting of SEQ ID NO:15-18. In some embodiments, the VH comprises the amino acid sequence of SEQ ID NO:11 and the VL comprises the amino acid sequence of SEQ ID NO:15. In some embodiments, the VH comprises the amino acid sequence of SEQ ID NO:10 and the VL comprises the amino acid sequence of SEQ ID NO:16.

In some embodiments, the antibody or fragment thereof is antibody-dependent cellular cytotoxicity (ADCC)-competent.

Methods are also provided. In one embodiment, a method of treating cancer in a patient in need thereof is provided, comprising administering to the patient the antibody or fragment thereof of the present disclosure. In some embodiments, the cancer is selected from the group consisting of bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer.

In another embodiment, provided is a method of treating or inhibiting infection in a patient in need thereof, comprising administering to the patient the antibody or fragment thereof of the present disclosure. In some embodiments, the infection is viral, bacterial, fungal, or parasite infection. In some embodiments, the infection is HIV infection.

Still further, one embodiment provides a method of treating cancer in a patient in need thereof, comprising: (a) treating a T cell, in vitro, with the antibody or fragment thereof of any one of claims 1-27; and (b) administering the treated T cell to the patient. In some embodiments, the method further comprises, prior to step (a), isolating the T cell from an individual. In some embodiments, the T cell is a tumor-infiltrating T lymphocyte, a CD4+ T cell, a CD8+ T cell, or the combination thereof.

Also provided, in one embodiment, is a method of detecting expression of TIGIT in a sample, comprising contacting the sample with the antibody or fragment thereof of the present disclosure under conditions for the antibody or fragment thereof to bind to the TIGIT, and detecting the binding which indicates expression of TIGIT in the sample.

Still further provided, in one embodiment, is a method of identifying a patient suitable for treatment with an anti-TIGIT therapy, comprising isolated a cell from the cancer patient and detecting the presence of a TIGIT protein with the antibody or fragment thereof of the present disclosure.

DETAILED DESCRIPTION

Definitions

Figure 1:
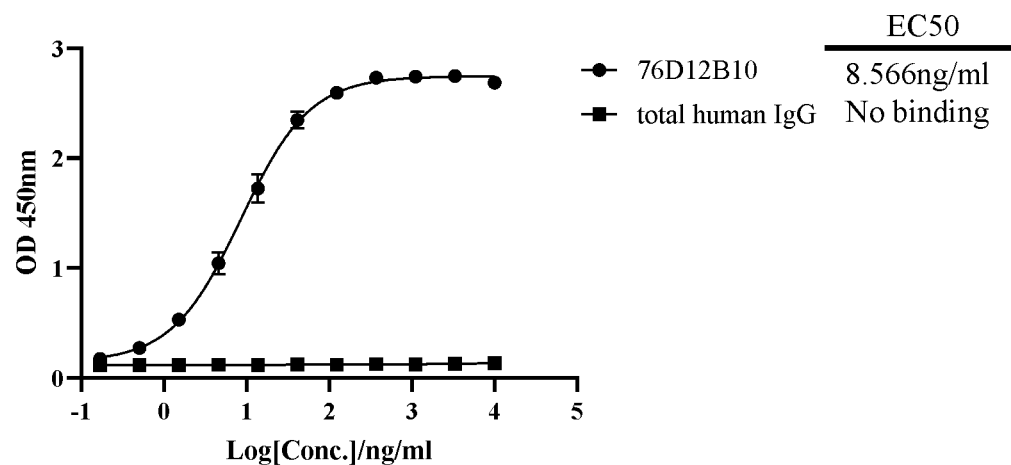
FIG. 1 shows the Elisa $EC_{50}$ for binding to human TIGIT protein for antibodies 76D12B10.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

As used herein, the term "antibody" encompasses various broad classes of polypeptides that can be distinguished biochemically. Those of skill in the art will appreciate that heavy chains are classified as gamma, mu, alpha, delta, or epsilon (γ, μ, α, δ, or ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight approximately 53,000-70,000 Daltons. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and $F(ab')_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein) Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (K, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, *J. Mol. Biol.*, 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those of skill in the art can routinely determine which residues comprise a particular CDR given the variable region amino acid sequence of the antibody.

|  | Kabat | Chothia |
|---|---|---|
| CDR-H1 | 31-35 | 26-32 |
| CDR-H2 | 50-65 | 52-58 |
| CDR-H3 | 95-102 | 95-102 |
| CDR-L1 | 24-34 | 26-32 |
| CDR-L2 | 50-56 | 50-52 |
| CDR-L3 | 89-97 | 91-96 |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein can be from any animal origin including birds and mammals. Preferably, the antibodies are human, murine, donkey, rabbit, goat, guinea pig, camel, llama, horse, or chicken antibodies. In some embodiments, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects (including human subject), that would benefit from administration of an antibody or composition of the present disclosure used, e.g., for detection, for a diagnostic procedure and/or for treatment.

Anti-TIGIT Antibodies

Like PD-1 and PD-L1, T cell immunoreceptor with Ig and ITIM domains (TIGIT) is frequently over-expressed on immune cells of cancer patients. TIGIT is considered an immune checkpoint, and the blockade thereof can lead to increased cell proliferation, cytokine production, and degranulation of TA-specific CD8+ T cells and TIL CD8+ T cells. Targeting TIGIT is also believed to enhance killing of HIV-infected cells.

Antibodies targeting TIGIT are being developed, showing certain clinical promises. The Bristol-Myers Squibb Company, for instance, disclosed an anti-TIGIT antibody 22G2 (see, e.g., US Patent Application Pub No: US20160176963) which was used as a control in the experimental examples. Another reference antibody used for comparison is Tiragolumab (RG6058), a fully human monoclonal antibody being developed by Roche for treating non-small cell lung cancer. There has been no approval of any molecules targeting TIGIT yet, however.

The present disclosure provides anti-TIGIT antibodies with high affinity and inhibitory activity on the human TIGIT protein. Importantly, as demonstrated in Example 7-8, the newly disclosed anti-TIGIT antibodies outperformed the control antibody Tiragolumab. Like Tiragolumab, the instant antibodies have potent binding affinity. Unexpectedly, however, the instant antibodies exhibited significantly greater activity in inhibiting the interaction between TIGIT and CD155 than both 22G2 and Tiragolumab (see, Example 8, FIG. 13). Therefore, the instant antibodies have superior properties than those already in development.

In some embodiments, therefore, the present disclosure provides an anti-TIGIT antibody or fragment thereof having binding specificity to the human TIGIT protein. In some embodiments, the antibody or fragment thereof includes (a) a VH CDR1 comprising SEQ ID NO: 1; (b) a VH CDR2 comprising SEQ ID NO: 2; (c) a VH CDR3 comprising SEQ ID NO: 3; (d) a VL CDR1 comprising SEQ ID NO: 4; (e) a VL CDR2 comprising SEQ ID NO: 5; and (f) a VL CDR3 comprising SEQ ID NO: 6. In some embodiments, the anti-TIGIT antibody or fragment thereof comprises: (a) a VH CDR1 of SEQ ID NO: 1, or a variant of SEQ ID NO: 1 having at least 75%, 80%, 85%, 90%, 95%, 98%, or 99% sequence identity to SEQ ID NO: 1; (b) a VH CDR2 of SEQ ID NO: 2, or a variant of SEQ ID NO: 2 having at least 75%, 80%, 85%, 90%, 95%, 98%, or 99% sequence identity to SEQ ID NO: 2; (c) a VH CDR3 of SEQ ID NO: 3, or a variant of SEQ ID NO: 3 having at least 75%, 80%, 85%, 90%, 95%, 98%, or 99% sequence identity to SEQ ID NO: 3; (d) a VL CDR1 of SEQ ID NO: 4, or a variant of SEQ ID NO: 4 having at least 75%, 80%, 85%, 90%, 95%, 98%, or 99% sequence identity to SEQ ID NO: 4; (e) a VL CDR2 of SEQ ID NO: 5; and (f) a VL CDR3 of SEQ ID NO: 6, or a variant of SEQ ID NO: 6 having at least 75%, 80%, 85%, 90%, 95%, 98%, or 99% sequence identity to SEQ ID NO: 6.

In some embodiments, the anti-TIGIT antibody or fragment thereof comprises: (a) a VH CDR1 of SEQ ID NO: 1, or a variant of SEQ ID NO: 1 having a single substitution, deletion or insertion relative to SEQ ID NO: 1; (b) a VH CDR2 of SEQ ID NO: 2, or a variant of SEQ ID NO: 2 having a single substitution, deletion or insertion relative to SEQ ID NO: 2; (c) a VH CDR3 of SEQ ID NO: 3, or a variant of SEQ ID NO: 3 having a single substitution, deletion or insertion relative to SEQ ID NO: 3; (d) a VL CDR1 of SEQ ID NO: 4, or a variant of SEQ ID NO: 4 having a single substitution, deletion or insertion relative to SEQ ID NO: 4; (e) a VL CDR2 of SEQ ID NO: 5, or a variant of SEQ ID NO: 5 having a single substitution, deletion or insertion relative to SEQ ID NO: 5; and (f) a VL CDR3 of SEQ ID NO: 6, or a variant of SEQ ID NO: 6 having a single substitution, deletion or insertion relative to SEQ ID NO: 6.

The substitutions disclosed herein, in some embodiments, are conservative substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in Tables 2-3, where a similarity score of 0 or higher (see Table A) indicates conservative substitution between the two amino acids.

TABLE A

Amino Acid Similarity Matrix

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |
| P | −3 | −1 | 6 | | | | | | | | | | | | | | | | | |
| G | −3 | 5 | | | | | | | | | | | | | | | | | | |
| C | 12 | | | | | | | | | | | | | | | | | | | |

TABLE B

Conservative Amino Acid Substitutions

| For Amino Acid | Substitution With |
| --- | --- |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib,β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

Examples of antibodies and fragments include those having a heavy chain variable region comprising an amino acid sequence selected from the group consisting of SEQ ID NO:7 and 9-14, or a peptide having at least 75%, 80%, 85%, 90%, 95%, 98%, or 99% sequence identity to an amino acid sequence selected from the group consisting of SEQ ID NO:7 and 9-14, while retaining the recited CDRs. Examples of such antibodies and fragments include those having a light chain variable region comprising an amino acid sequence selected from the group consisting of SEQ ID NO:8 and 15-18, or a peptide having at least 75%, 80%, 85%, 90%, 95%, 98%, or 99% sequence identity to an amino acid sequence selected from the group consisting of SEQ ID NO:8 and 15-18, while retaining the recited CDRs.

Examples of antibodies and fragments include those having a heavy chain variable region comprising an amino acid sequence selected from the group consisting of SEQ ID NO:9-14, or a peptide having at least 75%, 80%, 85%, 90%, 95%, 98%, or 99% sequence identity to an amino acid sequence selected from the group consisting of SEQ ID NO:9-14, while retaining the recited CDRs. Examples of such antibodies and fragments include those having a light chain variable region comprising an amino acid sequence selected from the group consisting of SEQ ID NO:15-18, or a peptide having at least 75%, 80%, 85%, 90%, 95%, 98%, or 99% sequence identity to an amino acid sequence selected from the group consisting of SEQ ID NO:15-18, while retaining the recited CDRs.

Examples of antibodies and fragments include those having a heavy chain variable region comprising the amino acid sequence of SEQ ID NO:11, or a peptide having at least 75%, 80%, 85%, 90%, 95%, 98%, or 99% sequence identity to the amino acid sequence of SEQ ID NO:11, while retaining the recited CDRs. Examples of such antibodies and fragments include those having a light chain variable region comprising the amino acid sequence of SEQ ID NO:15, or a peptide having at least 75%, 80%, 85%, 90%, 95%, 98%, or 99% sequence identity to the amino acid sequence of SEQ ID NO:15, while retaining the recited CDRs. An example antibody is Hu02.

Examples of antibodies and fragments include those having a heavy chain variable region comprising the amino acid sequence of SEQ ID NO:10, or a peptide having at least 75%, 80%, 85%, 90%, 95%, 98%, or 99% sequence identity to the amino acid sequence of SEQ ID NO:10, while retaining the recited CDRs. Examples of such antibodies and fragments include those having a light chain variable region comprising the amino acid sequence of SEQ ID NO:16, or a peptide having at least 75%, 80%, 85%, 90%, 95%, 98%, or 99% sequence identity to the amino acid sequence of SEQ ID NO:16, while retaining the recited CDRs. An example antibody is Hu06.

In some embodiments, also provided is an anti-TIGIT antibody or fragment that specifically binds to TIGIT competitively with any one of the anti-TIGIT antibodies or fragments described herein. In some embodiments, competitive binding may be determined using an ELISA assay. In some embodiments, the $K_d$ of the binding between the competing anti-TIGIT antibodies or fragments and TIGIT is about $10^{-5}$ M to about $10^{-12}$ M (such as about $10^{-7}$ M to about $10^{-12}$ M, or about $10^{-8}$ M to about $10^{-12}$ M). In some embodiments, the competing anti-TIGIT antibody or fragment is chimeric, human, partially humanized, or fully humanized.

It will also be understood by one of skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, 99%, or a range between any two of these values, identical to the starting sequence.

In some embodiments, the antibody comprises an amino acid sequence or one or more moieties not normally associated with an antibody. Exemplary modifications are described in more detail herein. For example, an antibody disclosed herein may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", Immunol. Rev. (52:119-58 (1982)).

Bi-Functional Molecules

TIGIT is an immune checkpoint. As an immune checkpoint inhibitor, an antibody or antigen-binding fragment specific to TIGIT can be combined with a second antigen-binding fragment specific to a tumor cell or an immune cell to generate a bispecific antibody.

In some embodiments, the immune cell is selected from the group consisting of a T cell, a B cell, a monocyte, a macrophage, a neutrophil, a dendritic cell, a phagocyte, a natural killer cell, an eosinophil, a basophil, and a mast cell. Molecules on the immune cell which can be targeted include, for example, CD33, CD47, CD73, Her2, EGFR, CEA VEGF, CD3, CD16, CD19, CD28, CD47, CD64, CD155, CD112, CD113, PVRL3, and PVRIG. Other examples include PD-1, CTLA-4, LAG-3 (also known as CD223), CD28, CD122, 4-1BB (also known as CD137), TIM3, OX-40 or OX4OL, CD40 or CD40L, LIGHT, ICOS/ICOSL, GITR/GITRL, CD27, VISTA, B7H3, B7H4, HEVM or BTLA (also known as CD272), and killer-cell immunoglobulin-like receptors (KIRs).

A "tumor antigen" refers to an antigenic substance produced in tumor cells, i.e., it triggers an immune response in the host. Tumor antigens are useful in identifying tumor cells and are potential candidates for use in cancer therapy. Normal proteins in the body are not antigenic. Certain proteins, however, are produced or overexpressed during tumorigenesis and thus appear "foreign" to the body. This may include normal proteins that are well sequestered from the immune system, proteins that are normally produced in extremely small quantities, proteins that are normally produced only in certain stages of development, or proteins whose structure is modified due to mutation.

An abundance of tumor antigens are known in the art and new tumor antigens can be readily identified by screening. Non-limiting examples of tumor antigens include EGFR, Her2, EpCAM, CD20, CD30, CD33, CD47, CD52, CD133, CD73, CEA, gpA33, Mucins, TAG-72, CIX, PSMA, folate-binding protein, GD2, GD3, GM2, VEGF, VEGFR, Integrin, αVβ3, α5β1, ERBB2, ERBB3, MET, IGF1R, EPHA3, TRAILR1, TRAILR2, RANKL, FAP and Tenascin.

Specific examples of bispecificity include, without limitation, TIGIT/LAG3, TIGIT/CD47, TIGIT/PD-1, TIGIT/PD-L1, TIGIT/CD155, TIGIT/CD112, TIGIT/CD113, TIGIT/PVRL3, TIGIT/PVRIG, and TIGIT/CD3.

Different format of bispecific antibodies are also provided. In some embodiments, each of the anti-TIGIT fragment and the second fragment each is independently selected from a Fab fragment, a single-chain variable fragment (scFv), or a single-domain antibody. In some embodiments, the bispecific antibody further includes a Fc fragment.

Bifunctional molecules that include not just antibody or antigen binding fragment are also provided. As a tumor antigen targeting molecule, an antibody or antigen-binding fragment specific to TIGIT, such as those described here, can be combined with an immune cytokine or ligand optionally through a peptide linker. The linked immune cytokines or ligands include, but not limited to, IL-2, IL-3, IL-4, IL-5, IL-6, IL-7, IL-10, IL-12, IL-13, IL-15, GM-CSF, TNF-α, CD40L, OX40L, CD27L, CD30L, 4-1BBL, LIGHT and GITRL. Such bi-functional molecules can combine the immune checkpoint blocking effect with tumor site local immune modulation.

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled.

In certain embodiments, the prepared antibodies will not elicit a deleterious immune response in the animal to be treated, e.g., in a human. In one embodiment, antigen-binding polypeptides, variants, or derivatives thereof of the disclosure are modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues.

De-immunization can also be used to decrease the immunogenicity of an antibody. As used herein, the term "de-immunization" includes alteration of an antibody to modify T-cell epitopes (see, e.g., International Application Publication Nos.: WO/9852976 A1 and WO/0034317 A2). For example, variable heavy chain and variable light chain sequences from the starting antibody are analyzed and a human T-cell epitope "map" from each V region showing the location of epitopes in relation to complementarity-determining regions (CDRs) and other key residues within the sequence is created. Individual T-cell epitopes from the T-cell epitope map are analyzed in order to identify alternative amino acid substitutions with a low risk of altering activity of the final antibody. A range of alternative variable heavy and variable light sequences are designed comprising combinations of amino acid substitutions and these sequences are subsequently incorporated into a range of binding polypeptides. Typically, between 12 and 24 variant antibodies are generated and tested for binding and/or function. Complete heavy and light chain genes comprising modified variable and human constant regions are then cloned into expression vectors and the subsequent plasmids introduced into cell lines for the production of whole antibody. The antibodies are then compared in appropriate biochemical and biological assays, and the optimal variant is identified.

The binding specificity of antigen-binding polypeptides of the present disclosure can be determined by in vitro assays such as immunoprecipitation, radioimmunoassay (RIA) or enzyme-linked immunoabsorbent assay (ELISA).

Examples of techniques which can be used to produce single-chain Fvs (scFvs) and antibodies include those described in U.S. Pat. Nos. 4,946,778 and 5,258,498; Huston et al., *Methods in Enzymology* 203:46-88 (1991); Shu et al., *Proc. Natl. Sci. USA* 90:1995-1999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art.

Humanized antibodies are antibody molecules derived from a non-human species antibody that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen-binding. These framework substitutions are identified by methods well known in the art, e.g., by modeling of the interactions of the CDR and framework residues to identify framework residues important for antigen-binding and sequence comparison to identify unusual framework residues at particular positions.

DNA encoding desired monoclonal antibodies can be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins.

Additionally, using routine recombinant DNA techniques, one or more of the CDRs of the antigen-binding polypeptides of the present disclosure, may be inserted within framework regions, e.g., into human framework regions to humanize a non-human antibody. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds to at least one epitope of a desired polypeptide, e.g., LIGHT. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present disclosure and within the skill of the art.

Treatments

As described herein, the antibodies, variants or derivatives of the present disclosure may be used in certain treatment and diagnostic methods.

The present disclosure is further directed to antibody-based therapies which involve administering the antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

In some embodiments, provided are methods for treating a cancer in a patient in need thereof. The method, in one embodiment, entails administering to the patient an effective amount of an antibody of the present disclosure. In some embodiments, at least one of the cancer cells (e.g., stromal cells) in the patient over-express TIGIT or is induced to express TIGIT.

Non-limiting examples of cancers include bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer.

Cellular therapies, and more specifically chimeric antigen receptor (CAR) T-cell (CAR-T) and NK cell (CAR-NK) therapies, are also provided in the present disclosure. A suitable T cell or NK cell can be used, that is put in contact with an anti-TIGIT antibody of the present disclosure (or alternatively engineered to express an anti-TIGIT antibody of the present disclosure). Upon such contact or engineering, the T cell or NK cell can then be introduced to a cancer patient in need of a treatment. The cancer patient may have a cancer of any of the types as disclosed herein. The T cell can be, for instance, a tumor-infiltrating T lymphocyte, a CD4+ T cell, a CD8+ T cell, or the combination thereof, without limitation.

In some embodiments, the T cell or NK cell was isolated from the cancer patient him- or her-self. In some embodiments, the T cell or NK cell was provided by a donor or from a cell bank. When the T cell or NK cell is isolated from the cancer patient, undesired immune reactions can be minimized.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracisternally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antigen-binding polypeptides or compositions of the disclosure locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

In a further embodiment, the compositions of the disclosure are administered in combination with an antineoplastic agent, an antiviral agent, antibacterial or antibiotic agent or antifungal agents. Any of these agents known in the art may be administered in the compositions of the current disclosure.

In another embodiment, compositions of the disclosure are administered in combination with a chemotherapeutic agent. Chemotherapeutic agents that may be administered with the compositions of the disclosure include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the disclosure are administered in combination with cytokines. Cytokines that may be administered with the compositions of the disclosure include, but are not limited to, IL-2, IL-3, IL-4, IL-5, IL-6, IL-7, IL-10, IL-12, IL-13, IL-15, anti-CD40, CD40L, and TNF-α.

In additional embodiments, the compositions of the disclosure are administered in combination with other therapeutic or prophylactic regimens, such as, for example, radiation therapy.

The anti-TIGIT antibodies of the present disclosure can be used, in some embodiments, together with an immune checkpoint inhibitor Immune checkpoints are molecules in the immune system that either turn up a signal (co-stimulatory molecules) or turn down a signal. Many cancers protect themselves from the immune system by inhibiting the T cell signal. An immune checkpoint inhibitor can help stop such a protective mechanism by the cell cells. An immune checkpoint inhibitor may target any one or more of the following checkpoint molecules, PD-1, PD-L1, CTLA-4, LAG-3 (also known as CD223), CD28, CD122, 4-1BB (also known as CD137), or BTLA (also known as CD272).

Programmed T cell death 1 (PD-1) is a trans-membrane protein found on the surface of T cells, which, when bound to programmed T cell death ligand 1 (PD-L1) on tumor cells, results in suppression of T cell activity and reduction of T cell-mediated cytotoxicity. Thus, PD-1 and PD-L1 are immune down-regulators or immune checkpoint "off switches". Example PD-1 inhibitor include, without limitation, nivolumab, (Opdivo) (BMS-936558), pembrolizumab (Keytruda), pidilizumab, AMP-224, MEDI0680 (AMP-514), PDR001, MPDL3280A, MEDI4736, BMS-936559 and MSB0010718C.

Programmed death-ligand 1 (PD-L1) also known as cluster of differentiation 274 (CD274) or B7 homolog 1 (B7-H1) is a protein that in humans is encoded by the CD274 gene. Non-limiting examples of PD-L1 inhibitor include Atezolizumab (Tecentriq), Durvalumab (MEDI4736), Avelumab (MSB0010718C), MPDL3280A, BMS935559 (MDX-1105) and AMP-224.

CTLA-4 is a protein receptor that downregulates the immune system. Non-limiting examples of CTLA-4 inhibitors include ipilimumab (Yervoy) (also known as BMS-734016, MDX-010, MDX-101) and tremelimumab (formerly ticilimumab, CP-675,206).

Lymphocyte-activation gene 3 (LAG-3) is an immune checkpoint receptor on the cell surface works to suppress an immune response by action to Tregs as well as direct effects on CD8+ T cells. LAG-3 inhibitors include, without limitation, LAG525 and BMS-986016.

CD28 is constitutively expressed on almost all human CD4+ T cells and on around half of all CD8 T cells. prompts T cell expansion. Non-limiting examples of CD28 inhibitors include TGN1412.

CD122 increases the proliferation of CD8+ effector T cells. Non-limiting examples include NKTR-214.

4-1BB (also known as CD137) is involved in T-cell proliferation. CD137-mediated signaling is also known to protect T cells, and in particular, CD8+ T cells from activation-induced cell death. PF-05082566, Urelumab (BMS-663513) and lipocalin are example CD137 inhibitors.

For any of the above combination treatments, the anti-TIGIT antibody can be administered concurrently or separately from the other anticancer agent. When administered separately, the anti-TIGIT antibody can be administered before or after the other anticancer agent.

In one embodiment, a method of treating or inhibiting infection in a patient in need thereof is provided, comprising administering to the patient an effective amount of the antibody or fragment thereof of the present disclosure. In some embodiments, the infection is viral infection (such as HIV infection), bacterial infection, fungal infection or infection by a parasite.

Infection is the invasion of an organism's body tissues by disease-causing agents, their multiplication, and the reaction of host tissues to these organisms and the toxins they produce. An infection can be caused by infectious agents such as viruses, viroids, prions, bacteria, nematodes such as parasitic roundworms and pinworms, arthropods such as ticks, mites, fleas, and lice, fungi such as ringworm, and other macroparasites such as tapeworms and other helminths. In one aspect, the infectious agent is a bacterium, such as Gram negative bacterium. In one aspect, the infectious agent is virus, such as DNA viruses, RNA viruses, and reverse transcribing viruses. Non-limiting examples of viruses include Adenovirus, Coxsackievirus, Epstein-Barr virus, Hepatitis A virus, Hepatitis B virus, Hepatitis C virus, Herpes simplex virus, type 1, Herpes simplex virus, type 2, Cytomegalovirus, Human herpesvirus, type 8, HIV, Influenza virus, Measles virus, Mumps virus, Human papillomavirus, Parainfluenza virus, Poliovirus, Rabies virus, Respiratory syncytial virus, Rubella virus, Varicella-zoster virus.

The antibodies of the present disclosure can also be used to treat an infectious disease caused by a microorganism, or kill a microorganism, by targeting the microorganism and an immune cell to effect elimination of the microorganism. In one aspect, the microorganism is a virus including RNA and DNA viruses, a Gram positive bacterium, a Gram negative bacterium, a protozoa or a fungus.

Diagnostic Methods

Over-expression of TIGIT is observed in certain tumor samples, and patients having TIGIT-over-expressing cells are likely responsive to treatments with the anti-TIGIT antibodies of the present disclosure. Accordingly, the antibodies of the present disclosure can also be used for diagnostic and prognostic purposes.

A sample that preferably includes a cell can be obtained from a patient, which can be a cancer patient or a patient desiring diagnosis. The cell be a cell of a tumor tissue or a tumor block, a blood sample, a urine sample or any sample from the patient. Upon optional pre-treatment of the sample, the sample can be incubated with an antibody of the present disclosure under conditions allowing the antibody to interact with a TIGIT protein potentially present in the sample. Methods such as ELISA can be used, taking advantage of the anti-TIGIT antibody, to detect the presence of the TIGIT protein in the sample.

Presence of the TIGIT protein in the sample (optionally with the amount or concentration) can be used for diagnosis of cancer, as an indication that the patient is suitable for a treatment with the antibody, or as an indication that the patient has (or has not) responded to a cancer treatment. For a prognostic method, the detection can be done at once, twice or more, at certain stages, upon initiation of a cancer treatment to indicate the progress of the treatment.

Compositions

The present disclosure also provides pharmaceutical compositions. Such compositions comprise an effective amount of an anti-TIGIT antibody or a fragment thereof disclosed herein, and a pharmaceutically acceptable carrier. In some embodiments, the composition further includes a second anticancer agent (e.g., an immune checkpoint inhibitor).

In a some embodiments, the term "pharmaceutically acceptable" means approved by a regulatory agency of the Federal or a state government or listed in the U.S. Pharmacopeia or other generally recognized pharmacopeia for use in animals, and more particularly in humans. A "pharmaceutically acceptable carrier" is generally a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In some embodiments, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1: Generation of Mouse Monoclonal Antibodies Against Human TIGIT

This example describes preparation of anti-human-TIGIT mouse monoclonal antibodies using the hybridoma technology.

Antigen: human TIGIT-Fc protein and human TIGIT overexpressed CHOK1 cell line (TIGIT-CHOK1 cell line).

Immunization: To generate mouse monoclonal antibodies to human TIGIT, Balb/c mice, SJL mice and Wistar Rat were first immunized with TIGIT-Fc protein. The immunized mice and Rat were respectively boosted with TIGIT-Fc fusion protein, CHO-K1/TIGIT stable cells and TIGIT-Fc protein. To select mice or rat producing antibodies that bound TIGIT protein, the serum of immunized mice was subjected to the antibody titer evaluation by ELISA. Briefly, microtiter plates were coated with human TIGIT protein at 0.5 µg/ml in ELISA coating buffer, 100 µl/well at 4° C. overnight, then blocked with 150 µl/well of 1% BSA. Dilutions of serum from immunized mice were added to each well and incubated for 1-2 hours at 37° C. The plates were washed with PBS/Tween and then incubated with anti-mouse IgG antibody conjugated with Horse Radish Peroxidase (HRP) or anti-rat IgG antibody conjugated with HRP. After washing, the plates were developed with TMB substrate and analyzed by spectrophotometer at OD 450 nm. Following 3 rounds of immunization, Immune responses were tested by serum ELISA against rhTIGIT protein and FACS against CHO-K1/TIGIT stable cell line while CHO-K1 parental cell line served as the negative control. Mice with sufficient titers of anti-TIGIT IgG were boosted with 25 µg human TIGIT-Fc protein after 4 rounds of immunization. The resulting mice were used for fusions. The hybridoma supernatants were tested for anti-TIGIT IgGs by ELISA.

Cell fusion and Hybridoma screening: Fusion was performed by electro fusion. Fused cells were plated into 50 plates for each fusion. The supernatants were screened by ELISA against recombinant human (rh) TIGIT Fc protein and counter screening antigen. Then, supernatants of positive clones were screened for function in blocking TIGIT binding to its ligand hCD155 by cell-based receptor blocking assay.

Subcloning and screening: positive primary clones from each fusion were subcloned by limiting dilution to ensure that the subclones were derived from a single parental cell. Supernatants of subclones were screened by cell based receptor blocking assay and affinity ranking.

Hybridoma clone 76D12B10 was selected for further analysis. The amino acid sequences of the variable regions of 76D12B10 are provided in Table 1 below.

TABLE I

Sequences of the variable regions of 76D12B10

| Name | Sequence | SEQ ID NO: |
|---|---|---|
| 76D12B10 VH | DVQLQESGPGMVKPSQSLSLTCTATGYSITSGY DWHWIRHFPGKKLEWMGFIRDSGSTVYNPSLKG RISITHDTSKNRFFLKLNSVTPEDTATYFCARG LFWYFDVWGTGTTVTVSS | 7 |
| 76D12B10VL | DIQMTQSPASLSASVGETVTITCRTSENIFSYL AWYQQKQGNSPQLLVHNTKTLAEGVPSRFSGSG SGTQFSLKISNLQPEDFGSYYCQHHYGNPLTFG AGTKLELK | 8 |

TABLE 1A

CDR sequences of 76D12B10

| 76D12B10 | Sequence | SEQ ID NO: |
|---|---|---|
| CDRH1 | SGYDWH | 1 |
| CDRH2 | FIRDSGSTVYNPSLKG | 2 |
| CDRH3 | GLFWYFDV | 3 |
| CDRL1 | RTSENIFSYLA | 4 |
| CDRL2 | NTKTLAE | 5 |
| CDRL3 | QHHYGNPLT | 6 |

Example 2: Antigen Binding Properties of Anti-TIGIT Mouse Monoclonal Antibodies

This example tested the binding properties of the anti-TIGIT mouse antibodies to the TIGIT proteins.

To evaluate the binding activity of 76D12B10, the chimeric mAb was subjected to ELISA test. Briefly, microtiter plates were coated with human TIGIT-His protein at 0.5 µg/ml in PBS, 100µl/well at 4° C. overnight, then blocked with 150 µl/well of 1% BSA. Three-fold dilutions of 76D12B10 antibodies starting from 10 µg/ml were added to each well and incubated for 1 hour at 37° C. The plates were washed with PBS/Tween and then incubated with Goat-anti-human IgG antibody conjugated with Horse Radish Peroxidase (HRP) for 30 mins at 37° C. After washing, the plates were developed with TMB substrate and analyzed by spectrophotometer at OD 450 nm. As shown in FIG. 1, 76D12B10 bound to human TIGIT with high affinity ($EC_{50}$=8.566 ng/ml).

Cross Species Activity

Figure 2:
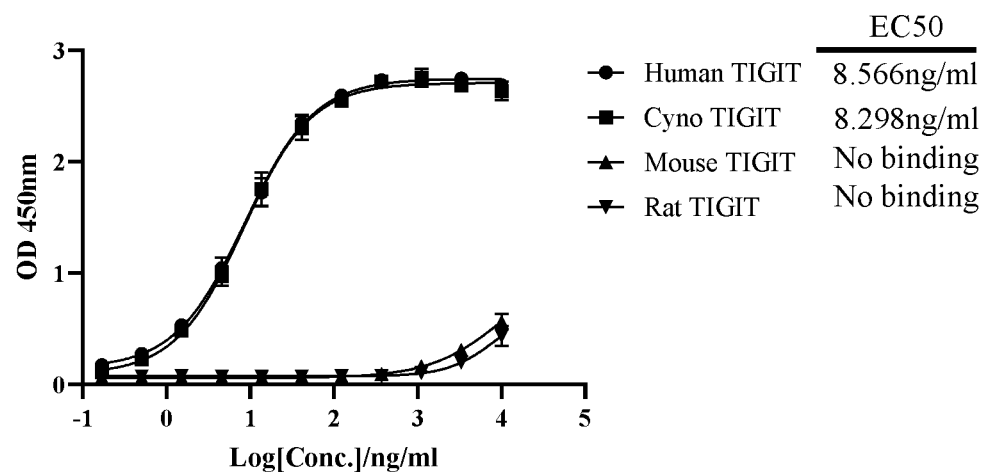
FIG. 2 shows that 76D12B10 antibodies can bind to cyno TIGIT with high affinity and cannot bind to rat or mouse TIGIT.

ELISA testing was carried out to evaluate the binding of chimeric antibodies to human, mouse, rat, and cyno TIGIT, respectively. Briefly, microtiter plates were coated with human, mouse, rat and cyno TIGIT proteins at 0.5 µg/ml in PBS, 100 µl/well at 4° C. overnight, then blocked with 150 µl/well of 1% BSA. Three-fold dilutions of chimeric antibodies or biotinylated chimeric antibodies starting from 10 µg/ml were added to each well and incubated for 1 hour at 37° C. The plates were washed with PBS/Tween and then incubated with Goat-anti-human IgG Fab antibody conjugated with Horse Radish Peroxidase (HRP) or Streptavidin-HRP for 30 mins at 37° C. After washing, the plates were developed with TMB substrate and analyzed by spectrophotometer at OD 450 nm. 76D12B10 antibodies bound to cyno TIGIT with high affinity ($EC_{50}$=8.298 ng/ml) and did not bind to rat or mouse TIGIT (FIG. 2 and Table 2).

TABLE 2

Cross species activity of 76D12B10

| | Human | Cyno | Rat | Mouse |
|---|---|---|---|---|
| EC50 of 76D12B10 | 8.566 ng/ml | 8.298 ng/ml | No binding | No binding |

Biacore Analysis of TIGIT Antibody

Figure 3:
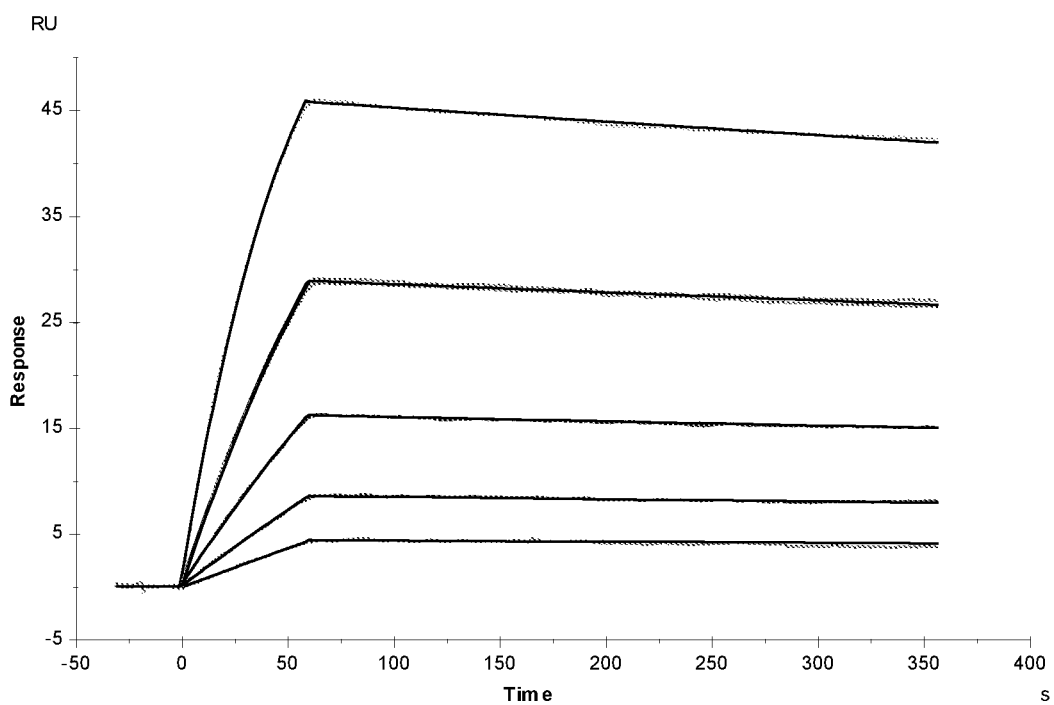
FIG. 3 shows the binding kinetics of 76D12B10 to recombinant TIGIT.

The binding of the 76D12B10 antibodies to recombinant TIGIT protein (human TIGIT-his tag) was tested with BIACORE™ using a capture method. The 76D12B10 mAbs was captured using CM5 chip. A series dilution of human TIGIT-his tag protein was injected over captured antibody for 1 min at a flow rate of 30 µl/min. The antigen was allowed to dissociate for 300 s. All the experiment were carried out on a Biacore T200. Data analysis was carried out using Biacore T200 evaluation software. The results are shown in FIG. 3 and Table 3 below.

TABLE 3

Binding of antibodies to recombinant TIGIT protein

| | TIGIT-His | | |
|---|---|---|---|
| Abs | ka (1/Ms) | kd (Ds) | KD (M) |
| 76D12B10 | 1.258E+6 | 3.259E−4 | 2.590E−10 |

Example 3. Humanization of the Mouse Antibodies

The 76D12B10 variable region genes were employed to create a humanized mAb (with an IgG1 N297A Fc fragment). In the first step of this process, the amino acid sequences of the VH and VL or VK of 76D12B10 were compared against the available database of human Ig gene sequences to find the overall best-matching human germline Ig gene sequences. For the light chain of 76D12B10, the closest human match was the A20/JK2 gene, and for the heavy chain the closest human match was the VH4-B/JH6 gene.

Humanized variable domain sequences of 76D12B10 were then designed where the CDRL1, L2 and L3 were grafted onto framework sequences of the A20/JK2 gene, and the CDRH1, H2, and H3 onto framework sequences of the VH4-B/JH6 gene. A 3D model was then generated to determine if there were any framework positions where replacing the mouse amino acid to the human amino acid could affect binding and/or CDR conformation. In the case of the heavy chain, V24A, S30T, G45K, I49M, V68I, V72H, and Y95F in the framework was involved in back-mutations. In the case of the light chain, V43S, I48V, and Y49H in the framework was involved in back-mutations (Tables 4 and 5).

TABLE 4

Humanized antibody sequences
(underlining indicates CDR;
bold/italic indicates back mutations)

| 76D12B10 | Sequence | SEQ ID NO: |
|---|---|---|
| VH mouse | DVQLQESGPGMVKPSQSLSLTCTATGYSITSGYDWHWI RHFPGKKLEWMGFIRDSGSTVYNPSLKGRISITHDTSK NRFFLKLNSVTPEDTATYFCARGLFWYFDVWGTGTTVT VSS | 7 |

TABLE 4 -continued

Humanized antibody sequences
(underlining indicates CDR;
bold/italic indicates back mutations)

| 76D12B10 | Sequence | SEQ ID NO: |
|---|---|---|
| VH-V0 | EVQLQESGPGLVKPSETLSLTCAVSGYSISSGYDWHWIRQPPGKGLEWIGFIRDSGSTVYNPSLKGRVTISVDTSKNQFSLKLSSVTAADTAVYYCARGLFWYFDVWGQGTTVTVSS | 9 |
| VH-V1 | EVQLQESGPGLVKPSETLSLTCAVSGYSISSGYDWHWIRQPPGKGLEWIGFIRDSGSTVYNPSLKGRVTIS*H*DTSKNQFSLKLSSVTAADTAVYYCARGLFWYFDVWGQGTTVTVSS | 10 |
| VH-V2 | EVQLQESGPGLVKPSETLSLTCAVSGYSISSGYDWHWIRQPPGKGLEWIGFIRDSGSTVYNPSLKGRITIS*H*DTSKNQFSLKLSSVTAADTAVYYCARGLFWYFDVWGQGTTVTVSS | 11 |
| VH-V3 | EVQLQESGPGLVKPSETLSLTCAVSGYSISSGYDWHWIRQPPGKGLEW*M*GFIRDSGSTVYNPSLKGRITIS*H*DTSKNQFSLKLSSVTAADTAVYYCARGLFWYFDVWGQGTTVTVSS | 12 |
| VH-V4 | EVQLQESGPGLVKPSETLSLTCA*A*SGYSI*T*SGYDWHWIRQPPGKGLEW*M*GFIRDSGSTVYNPSLKGRITIS*H*DTSKNQFSLKLSSVTAADTAVYYCARGLFWYFDVWGQGTTVTVSS | 13 |
| VH-V5 | EVQLQESGPGLVKPSETLSLTCA*A*SGYSI*T*SGYDWHWIRQPPGK*K*LEW*M*GFIRDSGSTVYNPSLKGRITIS*H*DTSKNQFSLKLSSVTAADTAVY*F*CARGLFWYFDVWGQGTTVTVSS | 14 |
| VL mouse | DIQMTQSPASLSASVGETVTITCRTSENIFSYLAWYQQKQGNSPQLLVHNTKTLAEGVPSRFSGSGSGTQFSLKISNLQPEDFGSYYCQHHYGNPLTFGAGTKLELK | 8 |
| VL V0 | DIQMTQSPSSLSASVGDRVTITCRTSENIFSYLAWYQQKPGKVPKLLIYNTKTLAEGVPSRFSGSGSGTDFILTISSLQPEDVATYYCQHHYGNPLTFGQGTKLEIK | 15 |
| VL V1 | DIQMTQSPSSLSASVGDRVTITCRTSENIFSYLAWYQQKPGKVPKLLI*H*NTKTLAEGVPSRFSGSGSGTDFILTISSLQPEDVATYYCQHHYGNPLTFGQGTKLEIK | 16 |
| VL V2 | DIQMTQSPSSLSASVGDRVTITCRTSENIFSYLAWYQQKPGKVPKLL*V*HNTKTLAEGVPSRFSGSGSGTDFILTISSLQPEDVATYYCQHHYGNPLTFGQGTKLEIK | 17 |
| VL V3 | DIQMTQSPSSLSASVGDRVTITCRTSENIFSYLAWYQQKPGK*S*PKLL*V*HNTKTLAEGVPSRFSGSGSGTDFILTISSLQPEDVATYYCQHHYGNPLTFGQGTKLEIK | 18 |

TABLE 5

Pairing of VH and VL for humanized antibodies

|  | VK.V0 | VK.V1 | VK.V2 | VK.V3 | VK |
|---|---|---|---|---|---|
| VH.V1 | Hu01 | Hu06 | Hu11 | Hu16 | |
| VH.V2 | Hu02 | Hu07 | Hu12 | Hu17 | |
| VH.V3 | Hu03 | Hu08 | Hu13 | Hu18 | |
| VH.V4 | Hu04 | Hu09 | Hu14 | Hu19 | |
| VH.V5 | Hu05 | Hu10 | Hu15 | Hu20 | |
| VH | | | | | Chimera |

Example 4: Antigen Binding Properties of the Humanized Antibodies

Binding to Recombinant Human TIGIT

Figure 4:
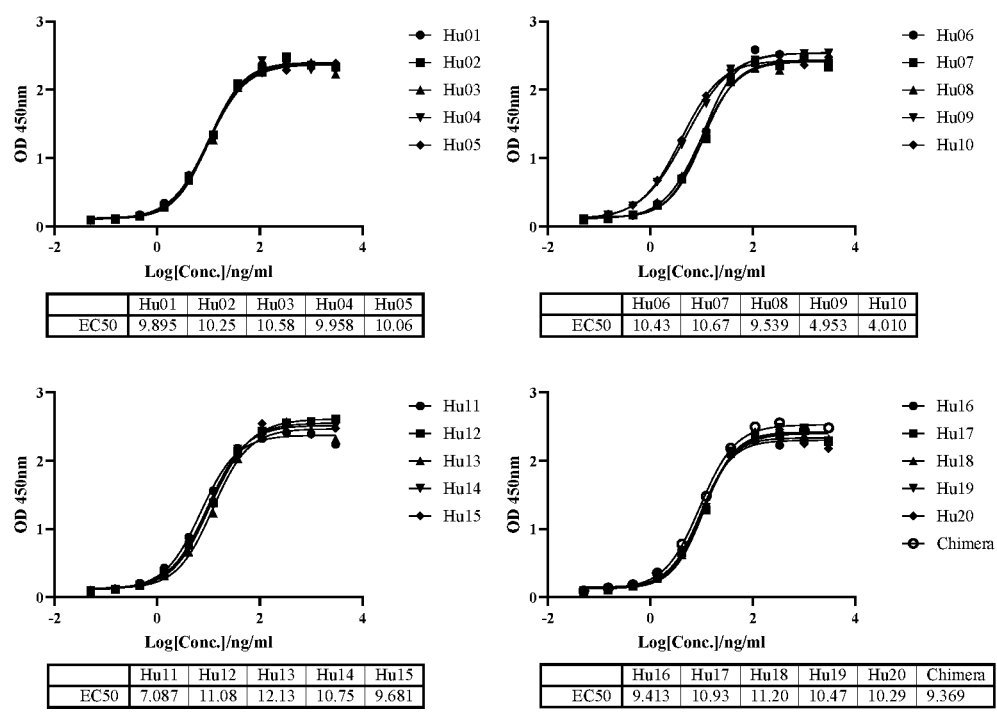
FIG. 4 shows that all tested humanized antibodies had comparable binding efficacy to human TIGIT in contrast to chimeric antibody.

To evaluate the antigen binding activity, the humanized antibodies were subjected to ELISA test. Briefly, microtiter plates were coated with human TIGIT-his protein at 0.5 µg/ml in PBS, 100 µl/well at 4° C. overnight, then blocked with 150 µl/well of 1% BSA. Three-fold dilutions of humanized antibodies starting from 3 µg/ml were added to each well and incubated for 1 hour at 37° C. The plates were washed with PBS/Tween and then incubated with Goat-anti-human IgG antibody conjugated with Horse Radish Peroxidase (HRP) for 30 mins at 37° C. After washing, the plates were developed with TMB substrate and analyzed by spectrophotometer at OD 450 nm. As shown in FIG. 4, all the humanized antibodies showed comparable binding efficacy to human TIGIT to the chimeric antibody.

Affinity Ranking of Humanized Antibodies by Biacore®

To explore the binding kinetics of the humanized antibodies, this example performed affinity ranking with Biacore®. As shown in Table 6, all of humanized antibodies from Hu02 to Hu20 showed excellent affinity, comparable to the chimeric antibody.

TABLE 6

Affinity ranking results of humanized antibodies

Human TIGIT His

| | ka (1/Ms) | Kd (1/s) | KD (M) |
|---|---|---|---|
| 76D12B10-Hu01 | 1.484E+6 | 1.041E−4 | 7.010E−11 |
| 76D12B10-Hu02 | 4.975E+6 | 9.744E−5 | 1.959E−11 |
| 76D12B10-Hu03 | 1.047E+7 | 1.497E−4 | 1.429E−11 |
| 76D12B10-Hu04 | 5.148E+6 | 9.848E−5 | 1.913E−11 |
| 76D12B10-Hu05 | 5.921E+6 | 9.747E−5 | 1.646E−11 |
| 76D12B10-Hu06 | 7.429E+6 | 1.009E−4 | 1.358E−11 |
| 76D12B10-Hu07 | 4.801E+6 | 8.928E−5 | 1.859E−11 |
| 76D12B10-Hu08 | 5.064E+6 | 9.729E−5 | 1.921E−11 |
| 76D12B10-Hu09 | 9.012E+6 | 1.255E−4 | 1.392E−11 |
| 76D12B10-Hu10 | 3.682E+6 | 9.791E−5 | 2.659E−11 |
| 76D12B10-Hu11 | 3.615E+6 | 9.208E−5 | 2.547E−11 |
| 76D12B10-Hu12 | 5.751E+6 | 1.400E−4 | 2.435E−11 |
| 76D12B10-Hu13 | 4.545E+6 | 1.279E−4 | 2.814E−11 |
| 76D12B10-Hu14 | 5.088E+6 | 9.968E−5 | 1.959E−11 |
| 76D12B10-Hu15 | 7.764E+6 | 1.050E−4 | 1.352E−11 |
| 76D12B10-Hu16 | 4.210E+6 | 9.131E−5 | 2.169E−11 |
| 76D12B10-Hu17 | 4.413E+6 | 8.348E−5 | 1.892E−11 |
| 76D12B10-Hu18 | 6.473E+6 | 8.719E−5 | 1.347E−11 |
| 76D12B10-Hu19 | 3.885E+6 | 8.961E−5 | 2.306E−11 |
| 76D12B10-Hu20 | 4.414E+6 | 9.444E−5 | 2.139E−11 |
| 76D12B10-Chimera | 1.130E+7 | 1.824E−4 | 1.614E−11 |

Binding to Recombinant Human TIGIT

Figure 5:
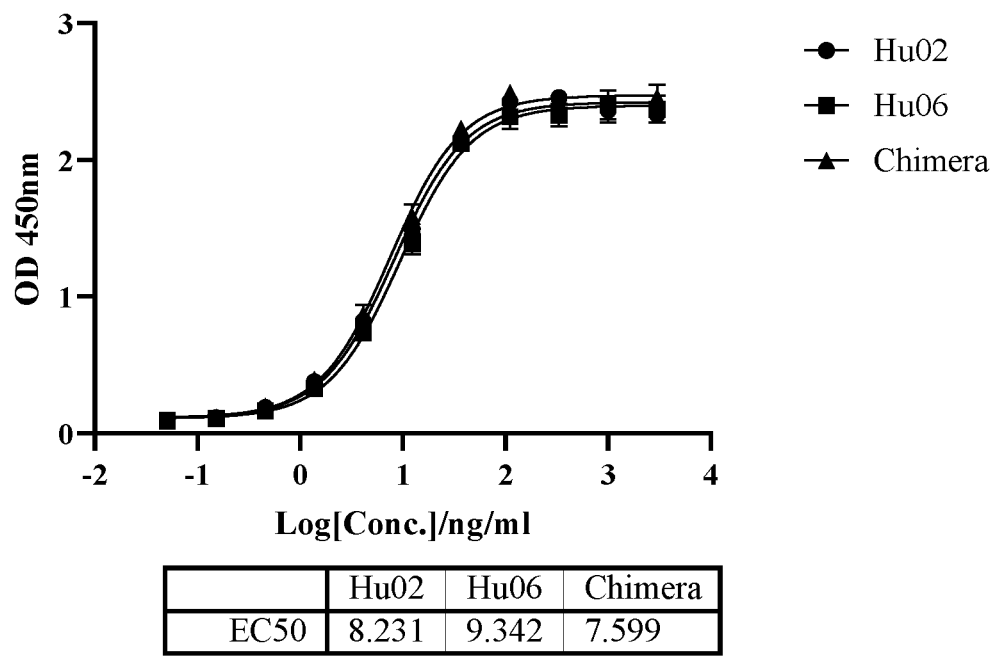
FIG. 5 shows that Hu02 and Hu06 antibodies had comparable binding efficacy to human TIGIT in contrast to chimeric antibody.

To evaluate the antigen binding activity, Hu02 and Hu06 were subjected to ELISA test. Briefly, microtiter plates were coated with human TIGIT-his protein at 0.5 µg/ml in PBS, 100 µl/well at 4° C. overnight, then blocked with 150 µl/well of 1% BSA. Three-fold dilutions of humanized antibodies starting from 3 µg/ml were added to each well and incubated for 1 hour at 37° C. The plates were washed with PBS/Tween and then incubated with Goat-anti-human IgG antibody conjugated with Horse Radish Peroxidase (HRP) for 0.5 hour at 37° C. After washing, the plates were developed with TMB substrate and analyzed by spectrophotometer at OD 450 nm. As shown in FIG. 5, Hu02 and Hu06 showed comparable binding efficacy to human TIGIT to the chimeric antibody.

Full Kinetic Affinity of Humanized Antibodies by Biacore®

Figure 6:
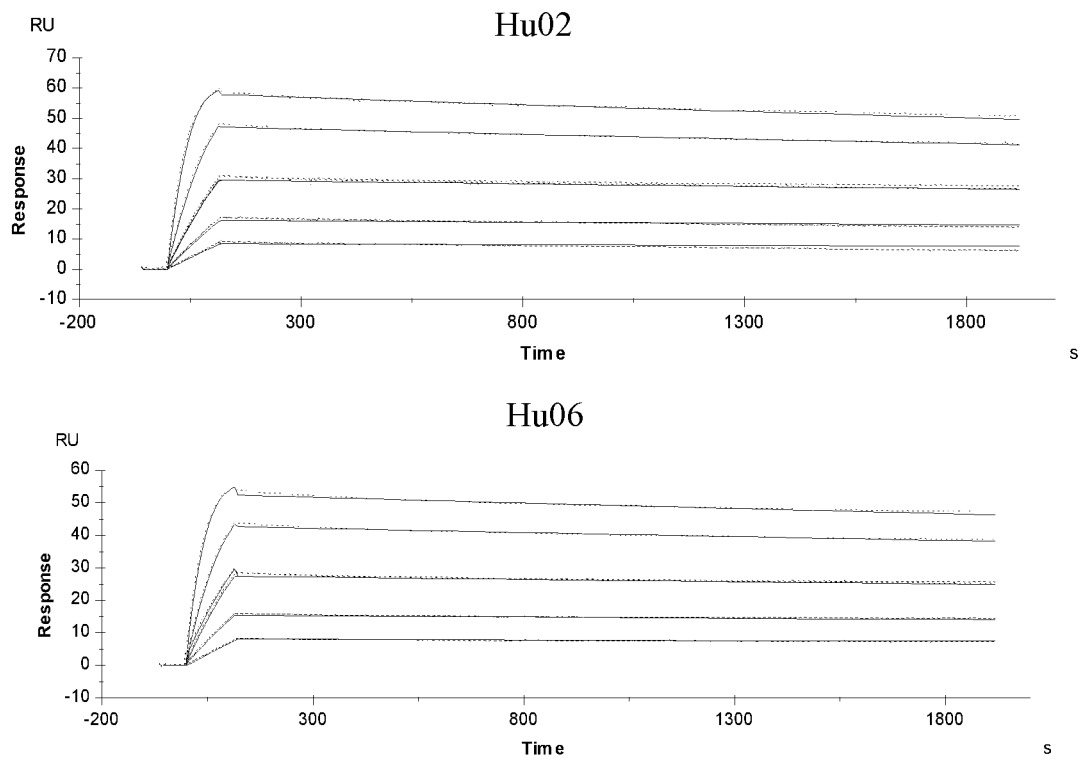
FIG. 6 shows that the binding kinetics of Hu02 and Hu06 antibodies to recombinant TIGIT.

The binding of the humanized antibodies to recombinant TIGIT protein (human TIGIT-his tag) was tested by BIACORE™ using a capture method. Hu02 and Hu06 mAbs were captured using Protein A chip. A serial dilution of human TIGIT-his tag protein was injected over captured antibody for 2 mins at a flow rate of 30 µl/min. The antigen was allowed to dissociate for 1800 s. All the experiment were carried out on a Biacore T200. Data analysis was carried out using Biacore® T200 evaluation software and is shown in FIG. 6 and Table 7.

TABLE 7

Affinity testing by_Biacore ®

Analyte hTIGIT-His

| Ligand | ka (1/Ms) | kd (1/s) | KD (M) |
|---|---|---|---|
| Hu02 | 2.005E+6 | 9.270E−5 | 4.623E−11 |
| Hu06 | 1.724E+6 | 7.180E−5 | 4.164E−11 |

Example 5: Functional Properties of Anti-TIGIT Humanized Antibodies

Blockade of Human TIGIT Protein Binding to CD155

To evaluate the blocking effects of Hu02 and Hu06 on recombinant human TIGIT to bind to its receptor CD155, an ELISA based receptor blocking assay was used.

Figure 7:
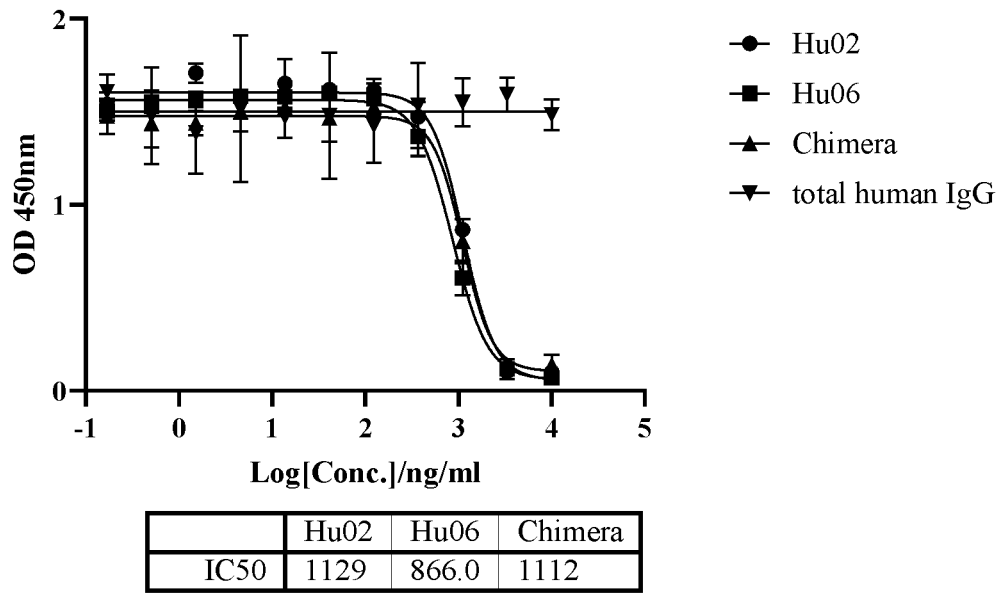
FIG. 7 shows that Hu02 and Hu06 antibodies can dose-dependently block TIGIT and CD155 interaction.

Briefly, microtiter plates were coated with human CD155-hFc protein at 5 µg/ml in PBS, 100 µl/well at 4° C. overnight, then blocked with 150 µl/well of 1% BSA. 50 µl biotin-labeled human TIGIT protein and 3-fold dilutions of Hu02 and Hu06 antibodies starting from 10 µg/ml at 50 µl were added to each well and incubated for 1 hour at 37° C. The plates were washed with PBS/Tween and then incubated with Streptavidin-HRP for 10 mins at 37° C. After washing, the plates were developed with TMB substrate and analyzed by spectrophotometer at OD 450 nm. As shown in FIG. 7, Hu02 and Hu06 efficiently inhibited the binding of human TIGIT protein to human CD155(Hu02 $IC_{50}$=1129 ng/ml, Hu06 $IC_{50}$=866.0 ng/ml), which was compared with 76D12B10 chimera ($IC_{50}$=1112 ng/ml).

In Vitro Effect of Anti-TIGIT Antibodies on Cell Based Functional Assay

To evaluate the functional activity of anti-TIGIT antibodies in blocking TIGIT signaling on T cells activation, an in vitro cell-based functional assay was used.

Figure 8:
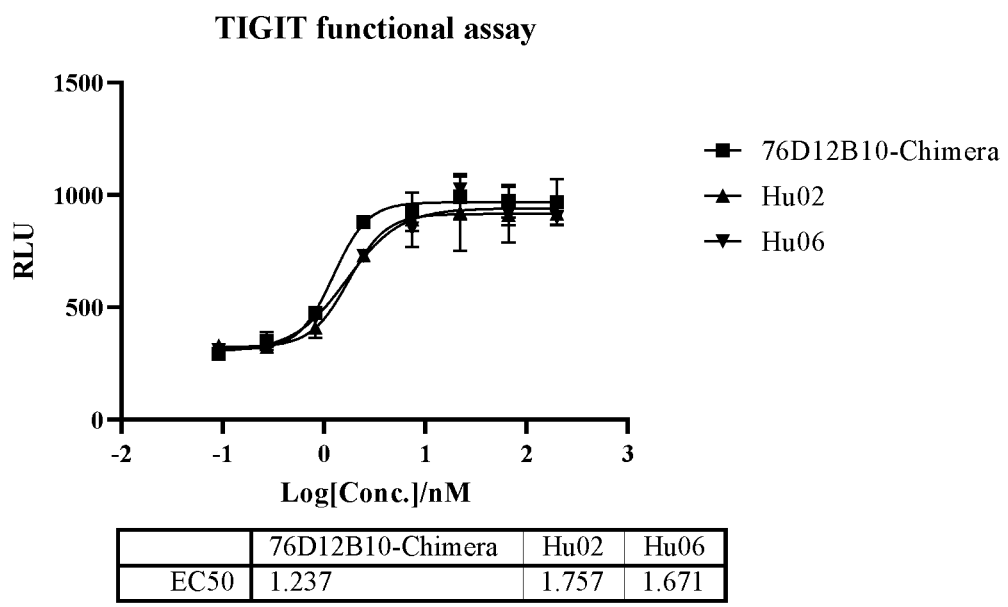
FIG. 8 shows that Hu02 and Hu06 antibodies dose-dependently inhibited the binding of CD155 to its receptor TIGIT by cell based functional assay.

Jurkat T NFAT cells are engineered to express human TIGIT and CD226, which can respond to both TCR activation and CD226 co-stimulation. Raji cells are engineered to express human CD155. Super antigen (Staphylococcal Enterotoxin) is designed to activate the T cell receptor (TCR) complex in an antigen-dependent manner. When the two cell types are co-cultured, TIGIT inhibits CD226 activation and NFAT Luciferase production. Addition of an anti-TIGIT antibody blocks the interaction of TIGIT with CD155 or inhibits the ability of TIGIT to prevent CD226 homodimerization, resulting in luciferase production. As shown in FIG. 8, Hu02 and Hu06 efficiently blockaded TIGIT and CD155 interaction (Hu02 $EC_{50}$=1.757 nM, Hu06 $EC_{50}$=1.671 nM), which was compared with 76D12B10 chimera ($EC_{50}$=1.237 nM).

Example 6: Efficacy in a MC38 Tumor Mouse Model

This example used a tumor mouse model to test the in vivo efficacy of the functional molecules.

MC38 cells resuspended in PBS were administered subcutaneously into right skin of B-hTIGIT humanized mice at a concentration of $5 \times 10^5$ cells in a volume of 0.1 mL. When the average tumor volume reached approximately 100 mm$^3$, the animals were randomly assigned to experimental groups according to the tumor volume, with 6 animals in each group. Total human IgG, Hu02-mIgG2a (Hu02-mouse IgG2a Fc) and Triagolumab-mIgG2a (Triagolumab-mouse IgG2a Fc) were administered twice every week by intraperitoneal injection. The dose was calculated based on the experimental animal's body weight at 3 mg/kg. Mice weight and tumor size were tested twice a week.

Figure 9:
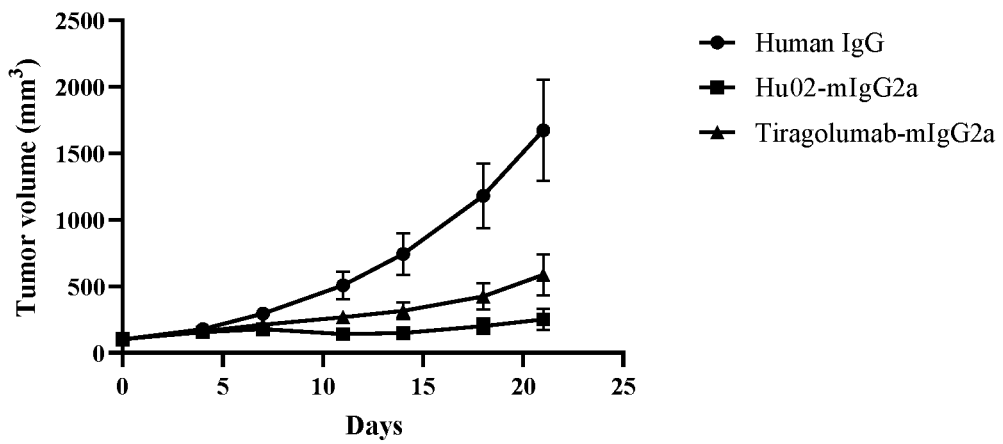
FIG. 9 shows that Hu02 antibodies had higher efficacy than Tiragolumab in an MC38 syngeneic mouse model in vivo.

The results are shown in FIG. 9. Compared with the Tiragolumab-mIgG2a group, Hu02-mIgG2a significantly inhibited tumor growth at a dose level of 3 mg/kg (p<0.05).

Example 7: Comparison of the TIGIT Antibodies

Binding to Recombinant Human TIGIT

Figure 10:
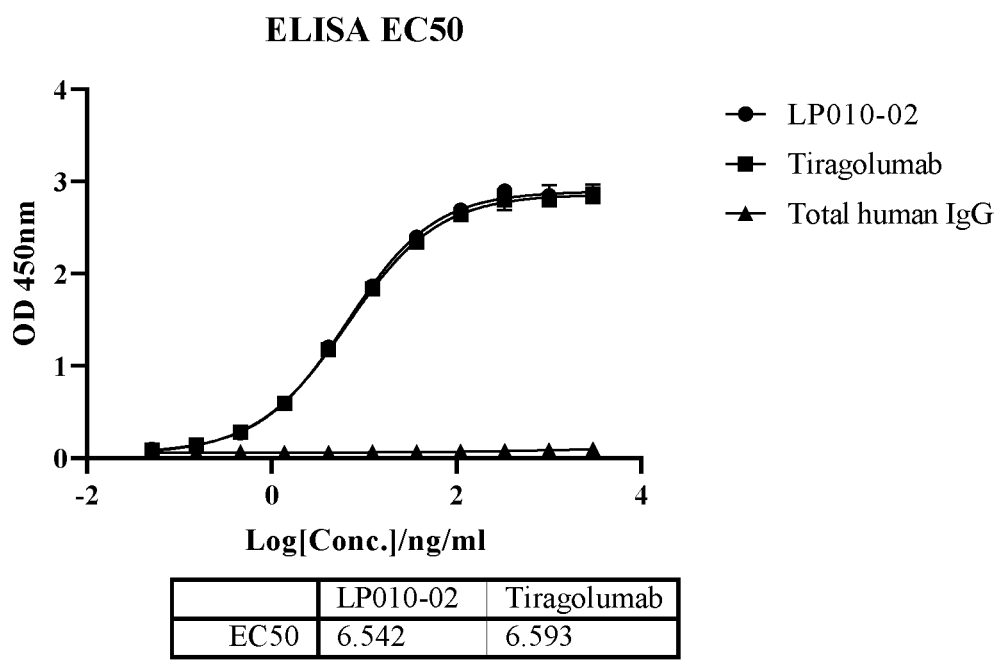
FIG. 10 shows that LP010-02 had comparable binding efficacy to human TIGIT protein in contrast to Tiragolumab.

To evaluate the antigen binding activity, LP010-02 (Hu02-human IgG1 Fc) and control antibody Tiragolumab (RG6058, Roche), which contains the same IgG1 Fc, were subjected to ELISA testing. Briefly, microtiter plates were coated with human TIGIT-his protein at 0.5 µg/ml in PBS, 100 µl/well at 4° C. overnight, then blocked with 150 µl/well of 1% BSA. Three-fold dilutions of humanized antibodies starting from 3 µg/ml were added to each well and incubated for 1 hour at 37° C. The plates were washed with PBS/Tween and then incubated with Goat-anti-human IgG antibody conjugated with Horse Radish Peroxidase (HRP) for 0.5 hour at 37° C. After washing, the plates were developed with the TMB substrate and analyzed by spectrophotometer at OD 450 nm. As shown in FIG. 10, LP010-02 and Tiragolumab showed comparable binding efficacy to human TIGIT.

Blockade of Human TIGIT Protein Binding to CD155

To evaluate the blocking effects of LP010-02 and Tiragolumab on recombinant human TIGIT to bind to its receptor CD155, an ELISA based receptor blocking assay was used.

Figure 11:
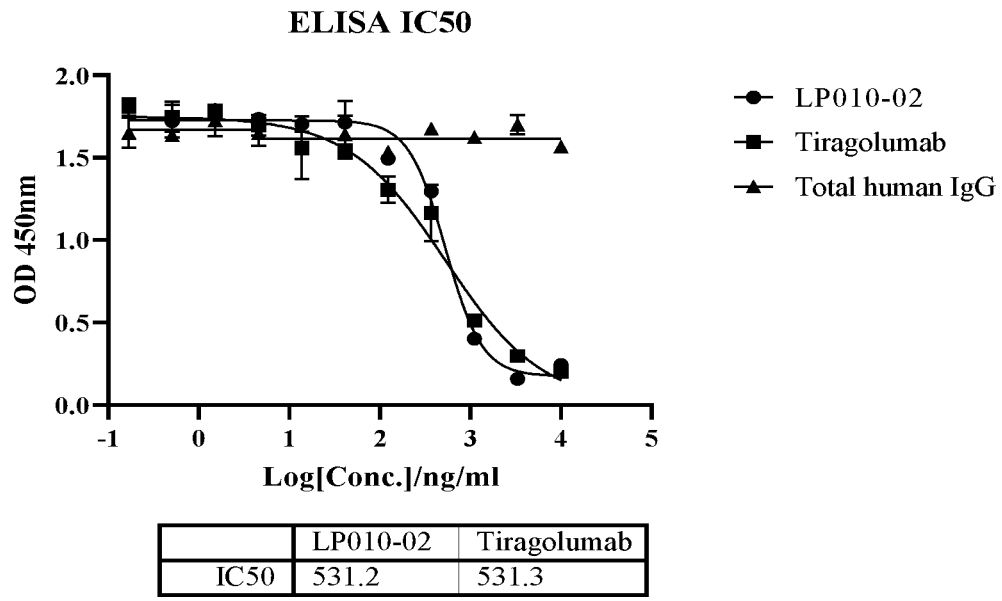
FIG. 11 shows that LP010-02 and Tiragolumab antibodies can efficiently inhibit the binding of human TIGIT protein to human CD155.

Briefly, microtiter plates were coated with human CD155-hFc protein at 5 µg/ml in PBS, 100 µl/well at 4° C. overnight, then blocked with 150 µl/well of 1% BSA. 50 µl biotin-labeled human TIGIT protein and 3-fold dilutions of LP010-02 and Tiragolumab antibodies starting from 10 µg/ml at 50 µl were added to each well. The plates were washed with PBS/Tween and then incubated with Streptavidin-HRP for 10 mins at 37° C. After washing, the plates were developed with the TMB substrate and analyzed by spectrophotometer at OD 450 nm. As shown in FIG. 11, LP010-02 and Tiragolumab efficiently inhibited the binding of human TIGIT protein to human CD155 (LP010-02 $IC_{50}$=531.2 ng/ml, Tiragolumab $IC_{50}$=531.3 ng/ml).

Binding to Human TIGIT Overexpressed Mammalian Cells

Figure 12:
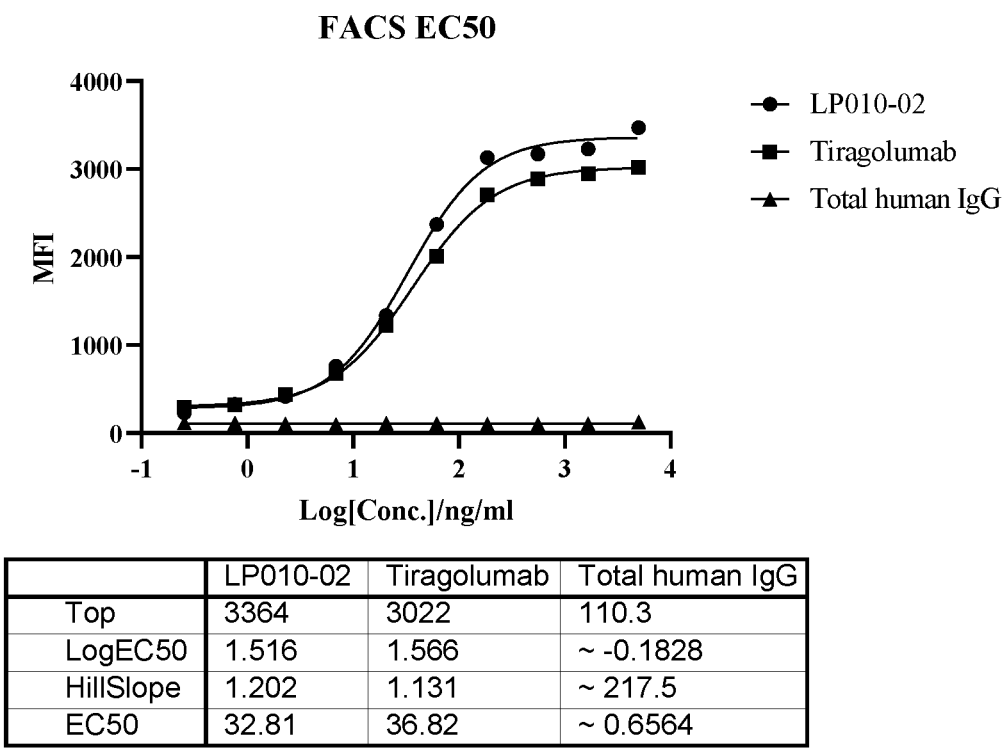
FIG. 12 shows that LP010-02 had better binding efficacy to human TIGIT protein overexpressed cells in contrast to Tiragolumab.

To evaluate the antigen binding property, the humanized antibodies were analyzed for their binding to human TIGIT overexpressed mammalian cells by FACS. Briefly, human TIGIT cells were firstly incubated with 3-fold serious diluted humanized antibodies starting at 5 µg/ml at 4° C. for 40 mins. After wash by PBS, the Alexa Fluor® 647 AffiniPure Goat Anti-Human IgG (H+L) antibody was added to each well and incubated at 4° C. for 30 mins. The MFI of Alexa Fluor® 647 were evaluated by FACSCanto. As shown in FIG. 12, LP010-02 and Tiragolumab showed better binding efficacy to human TIGIT expressed on mammalian cells (LP010-02 $EC_{50}$=32.81 ng/ml, Tiragolumab $EC_{50}$=36.82 ng/ml).

Example 8: Functional Assay for TIGIT/CD155 Blockade

The activities of the functional molecules in blocking TIGIT/CD155 interaction were measured with a bioluminescent cell-based assay in this example.

In this assay, when TIGIT-CD226-NFAT effector cells and Raji-CD155 target cells are co-cultured, TIGIT can bind to CD155 with higher affinity or destroy CD226 homodimerization and inhibit CD226 signal transduction in the presence of super antigen, thereby inhibiting the NFAT reporter gene activated by super antigen. Addition of an anti-TIGIT antibody (LP010-02, Tiragolumab and 22G2, containing the same human IgG1 Fc.) that blocks the TIGIT/CD155 interaction results in restoring of NFAT-mediated signal. 22G2 is an anti-TIGIT antibody (see, e.g., US Patent Application Pub No: US20160176963) being developed by The Bristol-Myers Squibb Company.

Figure 13:
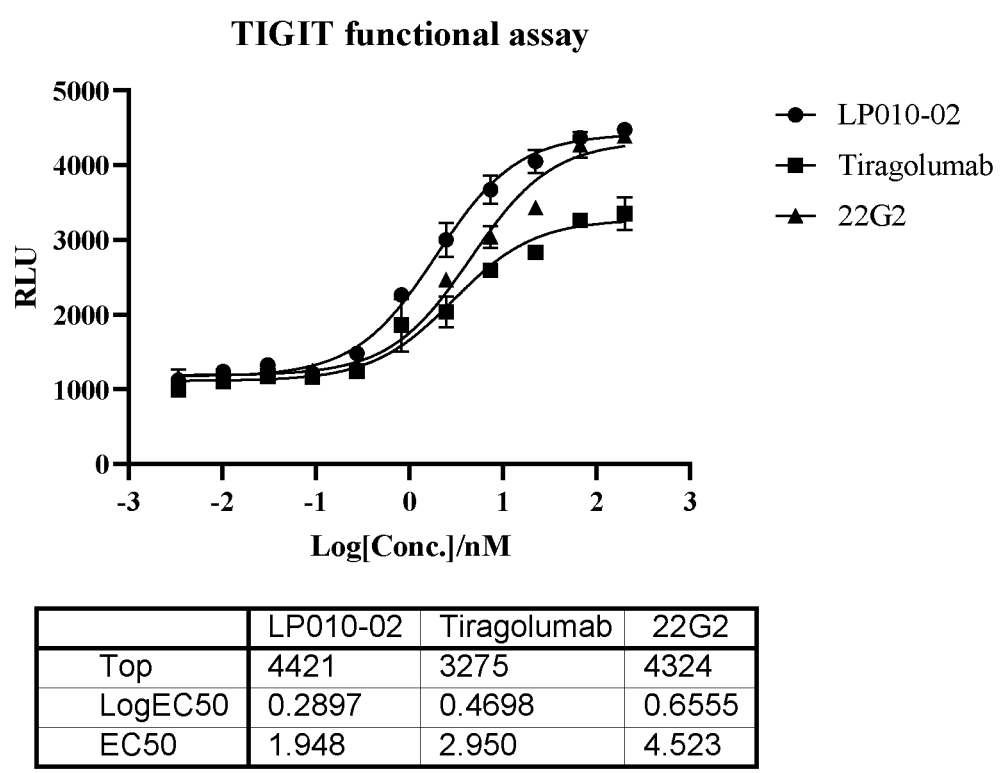
FIG. 13 shows that LP010-02 antibodies blocked TIGIT and CD155 interaction with higher activity than Tiragolumab and 22G2.

As shown in FIG. 13, LP010-02 blockaded TIGIT and CD155 interaction with higher activity than Tiragolumab and 22G2.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference

What is claimed is:

1. An antibody or antigen-binding fragment thereof, wherein the antibody or fragment thereof has specificity to a T cell immunoreceptor with Ig and ITIM domains (TIGIT) protein and comprises a heavy chain variable region (VH) comprising a VH CDR1 comprising the amino acid sequence of SEQ ID NO:1, a VH CDR2 comprising the amino acid sequence of SEQ ID NO:2, and a VH CDR3 comprising the amino acid sequence of SEQ ID NO:3, and a light chain variable region (VL) comprising a VL CDR1 comprising the amino acid sequence of SEQ ID NO:4, a VL CDR2 comprising the amino acid sequence of SEQ ID NO:5, and a VL CDR3 comprising the amino acid sequence of SEQ ID NO:6.

2. The antibody or fragment thereof of claim 1, further comprising a Fc fragment.

3. The antibody or fragment thereof of claim 2, wherein the Fc fragment is an human IgG1 Fc fragment.

4. The antibody or fragment thereof of claim 1, which is humanized.

5. The antibody or fragment thereof of claim 1, wherein the VH comprises an amino acid sequence selected from the group consisting of SEQ ID NO:9-14 and the VL comprises an amino acid sequence selected from the group consisting of SEQ ID NO:15-18.

6. The antibody or fragment thereof of claim 5, wherein the VH comprises the amino acid sequence of SEQ ID NO:11 and the VL comprises the amino acid sequence of SEQ ID NO:15.

7. The antibody or fragment thereof of claim 5, wherein the VH comprises the amino acid sequence of SEQ ID NO:10 and the VL comprises the amino acid sequence of SEQ ID NO:16.

8. The antibody or fragment thereof of claim 1, which is antibody-dependent cellular cytotoxicity (ADCC)-competent.

9. A bispecific antibody comprising a fragment of claim 1 and a second antigen-binding fragment having a second specificity.

10. The bispecific antibody of claim 9, wherein the second specificity is to a molecule on an immune cell or a tumor antigen.

11. The bispecific antibody of claim 9, wherein the second specificity is to a molecule selected from the group consisting of CD33, CD47, CD73, Her2, EGFR, CEA VEGF, CD155, CD112, CD113, PVRL3, PVRIG, CD3, CTLA-4, GITR, 4-1BB, PD-L1, PD-1, LAG-3, CD28, CD122, TIM3, OX-40, OX40L, CD40, CD40L, LIGHT, ICOS, ICOSL, GITR, GITRL, CD27, VISTA, B7H3, B7H4, HEVM, BTLA, KIR, and combinations thereof.

12. The bispecific antibody of claim 9, wherein the fragment and the second antigen-binding fragment each is independently selected from a Fab fragment or a single-chain variable fragment (scFv).

13. A composition comprising the antibody or fragment thereof of claim 1 and a pharmaceutically acceptable carrier.

14. One or more polynucleotides encoding the antibody or fragment thereof of claim 1.

15. An isolated cell comprising the one or more polynucleotide of claim 14.

16. A method of treating cancer in a patient in need thereof, comprising administering to the patient the antibody or fragment thereof of claim 1.

17. The method of claim 16, wherein the cancer is selected from the group consisting of bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer.

18. A method of treating or inhibiting infection in a patient in need thereof, comprising administering to the patient the antibody or fragment thereof of claim 1.

19. A method of treating cancer in a patient in need thereof, comprising (a) treating a T or NK cell, in vitro, with the antibody or fragment thereof of claim 1; and (b) administering the treated T or NK cell to the patient.

20. The method of claim 19, further comprising, prior to step (a), isolating the T or NK cell from an individual.

* * * * *